United States Patent [19]

Henning et al.

[11] Patent Number: 5,580,977
[45] Date of Patent: Dec. 3, 1996

[54] PROCESS FOR PREPARING LORACARBEF MONOHYDRATE

[75] Inventors: William C. Henning; Theodore R. Stout, both of Lafayette, India.

[73] Assignee: Eli Lilly and Company, Indianapolis, India.

[21] Appl. No.: 396,948

[22] Filed: Mar. 1, 1995

[51] Int. Cl.$^6$ ............................................. C07D 487/04
[52] U.S. Cl. ............................................. 540/205
[58] Field of Search ..................................... 540/205

[56] References Cited

U.S. PATENT DOCUMENTS

| | | |
|---|---|---|
| 3,502,663 | 3/1970 | Barnes . |
| 3,531,481 | 9/1970 | Pfeiffer . |
| 4,775,751 | 10/1988 | McShane . |
| 4,977,257 | 12/1990 | Eckrich et al. . |
| 5,352,782 | 10/1994 | Nist et al. . |
| 5,374,719 | 12/1994 | Plocharczyk et al. . |
| 5,399,686 | 3/1995 | Henning et al. ............... 540/205 |

FOREIGN PATENT DOCUMENTS

| | | |
|---|---|---|
| 0311366 | 4/1989 | European Pat. Off. . |
| 0369686 | 5/1990 | European Pat. Off. . |

OTHER PUBLICATIONS

Chemical Abstracts, vol. 116, No. 22, 1 Jun. 1992, Abstract No. 221407d.
Chemical Abstracts, vol. 119, No. 26, 27 Dec. 1993, Abstract No. 285163r.

*Primary Examiner*—Mukund J. Shah
*Assistant Examiner*—King Lit Wong
*Attorney, Agent, or Firm*—Janet McClain; David E. Boone

[57] ABSTRACT

The invention is directed to a crystalline anhydrate solvate of loracarbef, and also is directed to a process for preparing a crystalline monohydrate form of the compound of formula (I)

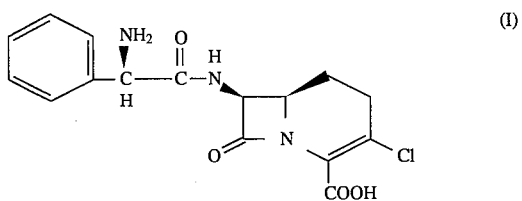

which comprises drying a crystalline isopropanolate form of the compound of formula (I) at a temperature of from about 50° C. to about 100° C. to provide a crystalline anhydrate form of the compound of formula (I); and exposing the crystalline anhydrate form of the compound of formula (I) to a relative humidity of from about 90 to about 100%.

15 Claims, No Drawings

PROCESS FOR PREPARING LORACARBEF MONOHYDRATE

BACKGROUND OF THE INVENTION

This invention relates to a process for preparing crystalline loracarbef monohydrate by drying loracarbef isopropanolate to provide loracarbef anhydrate and then hydrating the loracarbef anhydrate to provide loracarbef monohydrate.

The β-lactam antibiotic of the formula (I)

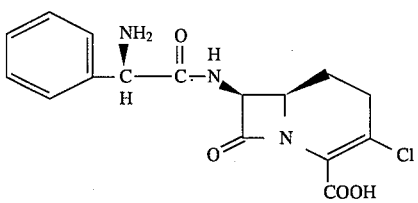

is a potent, orally active antibiotic known as loracarbef. The antibiotic is described, for example, in Hashimoto et al., U.S. Pat. Ser. No. 4,335,211.

Loracarbef has been isolated in various forms, including the crystalline monohydrate form, which is disclosed in European Patent Publication (EPA) 0,311,366. Other known solvate forms of the compound are disclosed in Eckrich et al., U.S. Pat. No. 4,977,257. The crystalline dihydrate form of loracarbef is disclosed in EPA 0,369,686.

As indicated in EPA 0,369,686, the crystalline monohydrate form of loracarbef may be prepared by first suspending loracarbef dihydrate in water and then effecting solution by the addition of acid followed by the adjustment of the pH with base, or by the addition of base followed by acid. The resultant loracarbef may be crystallized and then isolated by filtration. Hereinafter, this process will be referred to as "the filtration process."

Crystalline loracarbef monohydrate is a fine, "hair-like" crystal which results in a very slow filtration. The monohydrate crystals tend to form a mat on the filter which prevents or reduces the ability to complete filtration and which requires the crystals to be washed with water. Since loracarbef monohydrate is moderately soluble in water, (approximately 10 mg/ml), this washing decreases the yield.

The filtration process is considered a commercially unattractive process for preparing loracarbef monohydrate in light of the difficulties with the filtration step. Subsequently, it was discovered that crystalline loracarbef monohydrate could be produced more efficiently by exposing a crystalline isopropanolate form of loracarbef to a temperature of from about 50° C. to about 90° C. and a relative humidity of from about 60% to about 100%. Hereinafter, this process will be referred to as "the isopropanolate process." Since this process is a solid state conversion of loracarbef isopropanolate to loracarbef monohydrate, it could be effected without filtering the crystalline monohydrate, thus providing a more efficient process.

However, the isopropanolate process is also considered commercially unattractive because it yields loracarbef monohydrate in the form of a fine, fluffy powder with a density of approximately 0.2 g/ml. This density renders the bulk product, loracarbef monohydrate, very difficult to formulate. Since this compound is intended for pharmaceutical use, the ability to formulate the bulk product is critical. For loracarbef monohydrate, a density of greater than or equal to 0.5 g/ml is desired in order to facilitate the formulation of the bulk product. Thus, it was necessary to modify the isopropanolate process in order to obtain a bulk product with a sufficient density such that the product could be formulated for pharmaceutical use.

Another disadvantage of the isopropanolate process is that the resultant loracarbef monohydrate can contain up to 5% residual isopropanol (by weight). Since it is generally accepted that solvent content should be kept at a minimum in products intended for human use, most of this residual isopropanol must be removed from the final product. Typically, it is desirable to decrease the level of isopropanol to less than 1.0% (by weight).

The residual isopropanol may be removed from the loracarbef monohydrate by drying the crystals under reduced pressure of about 0 mm Hg to about 400 mmHg at a temperature of from about 25° C. to about 80° C. A consequence of the drying procedure is that some of the water in the loracarbef monohydrate crystal may also be removed. Thus, if the mixture is dried too much, it will affect the chemical makeup of the loracarbef monohydrate by reducing the water content although X-ray analysis indicates that the crystalline structure remains the same.

The removal of too much water during the drying process creates an additional problem since loracarbef monohydrate having less than approximately 5% water (by weight) will absorb water from the air during storage and further processing. If this rehydration occurs, the potency of the material will change such that an accurate dosage during the formulation process will not be obtained.

Accordingly, the present invention provides a facile conversion of loracarbef isopropanolate to loracarbef monohydrate that results in a commercially desirable form of the bulk product.

SUMMARY OF THE INVENTION

The present invention provides a crystalline anhydrate form of loracarbef.

The present invention provides a process for preparing a crystalline anhydrate form of the compound of formula (I)

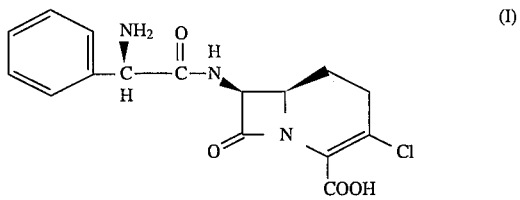

which comprises drying a crystalline isopropanolate form of the compound of formula (I) at a temperature of from about 50° C. to about 100° C.

The present invention also provides a process for preparing a crystalline monohydrate form of the compound of formula (I) which comprises exposing a crystalline anhydrate form of the compound of formula (I) to a relative humidity of from about 90 to about 100%.

The present invention also provides a process for preparing a crystalline monohydrate form of the compound of formula (I) having a bulk density of greater than or equal to 0.5 g/ml which comprises:

a) exposing a crystalline anhydrate form of the compound of formula (I) to a relative humidity of from about 90 to about 100% to provide a crystalline monohydrate form of the compound of formula (I) having a water content greater than or equal to 10%; and then b) drying the crystalline monohydrate at a temperature of from about 55° C. to about 75° C. at a pressure of from about 20 mbar to about 50 mbar.

In addition, the present invention provides a process for preparing a crystalline monohydrate form of the compound of formula (I) which comprises:

a) drying a crystalline isopropanolate form of the compound of formula (I) at a temperature of from about 50° C. to about 100° C. to provide a crystalline anhydrate form of the compound of formula (I); and b) exposing the crystalline anhydrate form of the compound of formula (I) to a relative humidity of from about 90 to about 100%.

Finally, the present invention provides a process for preparing a crystalline monohydrate form of the compound of formula (I) having a bulk density greater than or equal to 0.5 g/ml and a residual isopropanol content less than 1% (by weight) which comprises:

a) drying a crystalline isopropanolate form of the compound of formula (I) at a temperature of from about 50° C. to about 100° C. to provide a crystalline anhydrate form of the compound of formula (I);

b) exposing the crystalline anhydrate form of the compound of formula (I) to a relative humidity of from about 90 to about 100% to provide a crystalline monohydrate form of the compound of formula (I) having a water content greater than or equal to 10%; and then c) drying the crystalline monohydrate at a temperature of from about 55° C. to about 75° C. at a pressure of from about 20 mbar to about 50 mbar.

DETAILED DESCRIPTION OF THE INVENTION

The term "water content" refers to a quantitative measurement of the water content of a particular compound. Water content was measured in accordance with the Karl Fischer titration method.

The present invention is directed to a crystalline anhydrate solvate of the compound of formula (I):

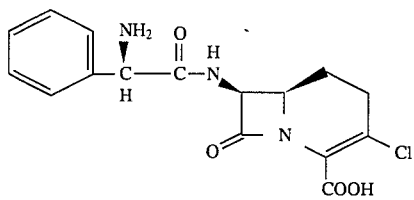

In the anhydrate solvate of the compound of formula (I), the C-2' asymmetric center has the R absolute configuration. Furthermore, the instant solvate may encompass the zwitterionic form of the compound of formula (I).

A preferred embodiment of the invention is the crystalline anhydrate solvate of loracarbef having the following X-ray powder diffraction pattern:

| Loracarbef anhydrate | |
|---|---|
| d | $I/I_1$ |
| 14.8536 | 53.96 |
| 10.0551 | 31.90 |
| 7.4652 | 100.00 |
| 6.7762 | 25.85 |
| 5.8288 | 87.78 |
| 5.1063 | 32.67 |
| 4.9546 | 32.40 |
| 4.8040 | 59.97 |
| 4.3038 | 34.39 |

-continued

| Loracarbef anhydrate | |
|---|---|
| d | $I/I_1$ |
| 3.9716 | 22.22 |
| 3.8515 | 18.12 |
| 3.7210 | 20.95 |
| 3.5890 | 8.50 |
| 3.4888 | 3.49 |
| 3.3798 | 46.57 |
| 3.2689 | 2.08 |
| 3.1825 | 3.59 |
| 2.9695 | 12.56 |
| 2.8837 | 4.10 |
| 2.8135 | 13.75 |
| 2.7670 | 41.37 |
| 2.6273 | 11.93 |

The diffraction pattern above was obtained with a copper radiation source in a Peltier cooled Si(Li) solid state detector. The tube voltage was set at 50 kV, the tube current was set at 40 mA, the aperture diaphragm was set at a 2 mm slit, the scattered radiation diaphragm was set at a 2 mm slit, the detector diaphragm had a 0.2 mm slit, the scanning rate for the step scan instrument was 0.02 degree/step two theta for 1.2 sec/step, and the scanning range was 4.0 to 35.0 degrees two theta. The background was electronically subtracted, the peak width was set at 0.3 and threshold at 3.0 for peak search.

It has been discovered that sequentially drying crystalline loracarbef isopropanolate at a temperature of from about 50° C. to about 100° C. to provide crystalline loracarbef anhydrate, and then exposing the loracarbef anhydrate to a relative humidity of from about 90 to 100% effects a facile solid state conversion of loracarbef isopropanolate to loracarbef monohydrate. This process represents an improved process for preparing loracarbef monohydrate which minimizes the amount of isopropanol in the final product without affecting the chemical composition of the loracarbef monohydrate and provides a product having a density greater than approximately 0.5 g/ml.

The isopropanolate form of loracarbef may be prepared using general procedures known in the art. For example, loracarbef isopropanolate may be readily prepared by suspending loracarbef in isopropanol or aqueous isopropanol and forming a solution. A solution is usually effected by the addition of a base or an acid. The desired isopropanolate may then be precipitated by the adjustment of the pH to approximately 5.8 to 6.2 by using an acid (for example, hydrochloric acid, hydrobromic acid or sulfuric acid) or a base (for example, triethylamine), respectively. The solution is usually prepared at a temperature of from about 20° C. to about 25° C. The isopropanolate may be isolated by procedures known in the art, for example, by filtration.

The solid state conversions of loracarbef isopropanolate to loracarbef anhydrate and of loracarbef anhydrate to loracarbef monohydrate must be effected sequentially in order to produce the desired result, that is, to produce loracarbef monohydrate with less than 1.0% isopropanol and without decreasing the water content. The conversion of the isopropanolate form to the anhydrate form is typically carried out at a temperature of from about 50° C. to about 100° C. A preferred temperature range is from about 55° C. to about 65° C. A further preferred temperature range is from about 63° C. to about 65° C.

The conversion of the anhydrate form to the monohydrate form is typically carried out at a relative humidity of from about 90 to about 100%. A preferred humidity range is from about 95 and 100%. Preferably, the conversion is effected at a relative humidity of 100%.

The following Examples further illustrate specific aspects of the present invention.

EXAMPLE 1

Loracarbef Isopropanolate

Isopropyl alcohol (660.0 ml), deionized water (67.0 ml), loracarbef bis(DMF)solvate (50.0 g) and hydrochloric acid (15.6 g) are combined and stirred at a temperature of 20°–25° C. If necessary, additional hydrochloric acid may be added to complete dissolution. Deionized water (10.0 ml) and activated carbon (2.0 g) are added to the mixture. The resultant reaction mixture is stirred for one hour and then the mixture is filtered to remove the carbon. Ammonia (28%, 12.6 g) is added, over at least 2 hours, to the filtrate in order to precipitate the isopropanolate, and the resultant slurry is filtered. The filter cake is washed with 127.0 ml of isopropanol, followed by a water wash (85.0 ml) and the wet cake is dried under vacuum at 40°–45° C. to provide the titled product.

EXAMPLE 2

Loracarbef Monohydrate

A Kugelrohr distillation apparatus is set up, consisting of a Kugelrohr oven with a time proportioning temperature controller, Type J thermocouple, 300 mm Allihn condenser attached to a constant temperature bath, a Kugelrohr distillation agitation motor and a Büchi pressure controller. A sample of loracarbef isopropanolate is charged to the 300 mm Allihn condenser. Deionized water (200 g) is charged to a 1 L., 1-neck, round bottom flask. The flask is in the Kugelrohr oven and connected to the condenser. The system's pressure is reduced to approximately 300 mbar. The jacket on the condenser is heated to 75° C. with a constant temperature bath. The Kugelrohr oven is heated to 65° C. The system's pressure is further reduced to 250 mbar and the isopropanolate is subjected to a relative humidity of 100% with agitation for approximately 6 to 8 hours. The oven and condenser are cooled to 20°–25° C. The system is vented to atmospheric pressure. The hydrated product is removed and placed in a vacuum oven at 40°–45° C. The product is dried overnight under full vacuum with a slight nitrogen sweep.

EXAMPLE 3

Loracarbef Isopropanolate

Loracarbef bis(DMF)solvate (70.50 g, 50.05 base g), isopropanol (520.0 g) and deionized water (88.8 g) (the original charge plus the carbon slurry amount of water) are charged to a 2 L jacketed 3-neck round bottom flask. Hydrochloric acid is then charged to the slurry to completely dissolve the solvate. Dissolution is complete at pH 0.90.

To the solution is charged activated carbon powder (2.0 g). The flask contents are stirred for approximately one hour at 20°–25° C. and then filtered over a 9 cm Büchner funnel pre-coated with a filter aid, such as Hyflo. The filtrate is returned to the jacketed flask and ammonia (28%, 12.7 g), is added dropwise over four hours via a syringe pump. Crystal size is large which is consistent with previous isopropanolate material.

The slurry is stirred for approximately one hour at 20°–25° C. and filtered over Whatman #1 filter paper (filtration time: 2:04 min). The wet cake is washed with isopropanol and water. The washed material is dried overnight in a vacuum oven at 40°–45° C. under full vacuum and a nitrogen sweep.

EXAMPLE 4

Loracarbef Isopropanolate

Isopropanol (440 L), deionized water (25 L), hydrochloric acid (10 kg), and loracarbef bis(DMF) solvate (42.3 kg) are combined in a tank. The tank walls are then rinsed with 22 L of deionized water. The mixture is stirred for 15 minutes and hydrochloric acid in 500 g increments is added to complete solution. A total of 2 kilograms of hydrochloric acid is added until disolution is completed, and the mixture is at pH 0.7.

Activated carbon (1.5 kg) slurried in 6 L of water is added to the tank and the mixture is stirred for 20 minutes and then filtered. The tank is rinsed with 10 L of deionized water. Ammonia (28%), is added until the solution is at pH 5.8–6.2. The resultant crystallized isopropanolate is filtered and washed with isopropyl alcohol. The filter cake is dried under a vacuum at a temperature of from about 42° C. to about 48° C.

EXAMPLE 5

Loracarbef Monohydrate

The material obtained in Example 4 is converted to loracarbef monohydrate using the isopropanolate process by setting the drier temperature to between 65° C. and 75° C., setting the vacuum control on the drier to 4 psia, and injecting steam into the drier to maintain a humidity in the range of 95 to 100%. After approximately one hour at these conditions, some of the content of the drier is cooled and a sample is taken. The conditions for conversion to loracarbef monohydrate, above, are set in place for three hours at which time indications are that conversion of the loracarbef monohydrate is complete. The material is then dried at full vacuum (0.7 psia) at 45° C. for approximately eight hours.

EXAMPLE 6

Loracarbef Anhydrate

Loracarbef isopropanolate wet cake (100 g) was placed in a fluid bed dryer and dried for approximately three hours at a temperature of from about 63° C. to about 65° C. with an air flow (blower setting 4) and agitator speed of 70 revolutions per minute (RPM). When the drying was substantially complete, analysis of the resultant crystalline solid indicated a residual isopropanol content of 0.9%. The crystalline solid was identified as loracarbef anhydrate using X-ray crystallography.

EXAMPLE 7

Loracarbef Anhydrate

Loracarbef isopropanolate wet cake (2.5 kg) was placed in a rotary vacuum dryer (0.85 cubic foot) equipped with an atomizing nozzle and dried for approximately 12.5 hours at a pressure of about 30 mbar and a jacket recirculating temperature of about 70° C. When the drying was substantially complete, analysis of the resultant crystalline solid indicated a residual isopropanol content of 0.55%.

EXAMPLE 8

Loracarbef Monohydrate

The rotary vacuum dryer containing the loracarbef anhydrate obtained in Example 7 was used in this Example. First, the jacket recirculating temperature was decreased to 30° C. and then water was added via the atomizing nozzle (water flow: 0.7 ml/min. and air flow to nozzle: approximately 15 standard cubic feet/minute (SCFM)) for approximately twelve hours. The resultant crystalline solid had a water content of 9.4% and was identified as loracarbef monohydrate using X-ray crystallography.

The crystalline solid was further dried in the rotary vacuum dryer at 65° C. and a pressure of 30 mbar to provide a product having a water content of 5.3% and a bulk density of 0.21 g/ml.

EXAMPLE 9

Loracarbef Monohydrate

Loracarbef isopropanolate wet cake (1.0 kg) was placed in a rotary vacuum dryer (0.85 cubic foot) equipped with an atomizing nozzle and dried for approximately ten hours at a pressure of about 40 mbar and a jacket recirculating temperature of about 70° C. When the drying was substantially complete, analysis of the resultant crystalline solid indicated a residual isopropanol content of 0.70%.

Next, the jacket recirculating temperature was decreased to 50° C. and then water was added via the atomizing nozzle (water flow: 3.0 ml/min. and air flow to nozzle: approx. 20 SCFM) for approximately twelve hours. When the water content of the resultant crystalline solid reached 22% (approximately 385 ml of water added), the jacket recirculating temperature was increased to approximately 70° C. and the pressure was adjusted to approximately 40 mbar and the solid was dried to provide the desired titled product with a water content of 5.2% and a bulk density of 0.43 g/ml. The crystalline solid was identified as loracarbef monohydrate using X-ray crystallography.

We claim:

1. A process for preparing a crystalline anhydrate form of the compound of formula (I)

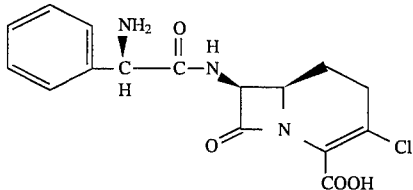

(I)

which comprises drying a crystalline isopropanolate form of the compound of formula (I) at a temperature of from about 50° C. to about 100° C.

2. A process as recited in claim 1 wherein said temperature is from about 55° C. to about 65° C.

3. A process as recited in claim 2 wherein said temperature is from about 63° C. to about 65° C.

4. A process for preparing a crystalline monohydrate form of the compound of formula (I) which comprises exposing a crystalline anhydrate form of the compound of formula (I) to a relative humidity of from about 90 to about 100%.

5. A process as recited in claim 4 wherein said relative humidity is from about 95 to about 100%.

6. The process as recited in claim 5 wherein said relative humidity is about 100%.

7. A process for preparing a crystalline monohydrate form of the compound of formula (I) having a bulk density of greater than or equal to 0.5 g/ml which comprises:

a) exposing a crystalline anhydrate form of the compound of formula (I) to a relative humidity of from about 90 to about 100% to provide a crystalline monohydrate form of the compound of formula (I) having a water content greater than or equal to 10%; and then b) drying the crystalline monohydrate at a temperature of from about 55° C. to about 75° C. at a pressure of from about 20 mbar to about 50 mbar.

8. The process as recited in claim 7 wherein said relative humidity is about 100%.

9. The process as recited in claim 8 wherein said relative humidity is about 100%, said temperature is from about 65° C. to about 75° C., and said pressure is from about 30 mbar to about 40 mbar.

10. A process for preparing a crystalline monohydrate form of the compound of formula (I) which comprises:

a) drying a crystalline isopropanolate form of the compound of formula (I) at a temperature of from about 50° C. to about 100° C. to provide a crystalline anhydrate form of the compound of formula (I); and b) exposing the crystalline anhydrate form of the compound of formula (I) to a relative humidity of from about 90 to about 100%.

11. A process as recited in claim 10 wherein said temperature is from about 55° C. to about 65° C. and said relative humidity is about 100%.

12. A process as recited in claim 11 wherein said temperature is from about 63° C. to about 65° C. and said relative humidity is about 100%.

13. A process for preparing a crystalline monohydrate form of the compound of formula (I) having a bulk density greater than or equal to 0.5 g/ml and a residual isopropanol content less than 1% (by weight) which comprises:

a) drying a crystalline isopropanolate form of the compound of formula (I) at a temperature of from about 50° C. to about 100° C. to provide a crystalline anhydrate form of the compound of formula (I);

b) exposing the crystalline anhydrate form of the compound of formula (I) to a relative humidity of from about 90 to about 100% to provide a crystalline monohydrate form of the compound of formula (I) having a water content greater than or equal to 10%; and then c) drying the crystalline monohydrate at a temperature of from about 55° C. to about 75° C. at a pressure of from about 20 mbar to about 50 mbar.

14. A process as recited in claim 13 wherein said temperature in step a) is from about 55° C. to about 65° C., said relative humidity is about 100%, said temperature in step c) is from about 65° C. to about 75° C., and said pressure is from about 30 mbar to about 40 mbar.

15. A process as recited in claim 14 wherein said temperature in step a) is from about 63° C. to about 65° C., said relative humidity is about 100%, said temperature in step c) is from about 65° C. to about 75° C., and said pressure is from about 30 mbar to about 40 mbar.

* * * * *